United States Patent

Baba et al.

[11] 4,217,223
[45] Aug. 12, 1980

[54] GEL PERMEATION CHROMATOGRAPH SYSTEM

[75] Inventors: Nobuyuki Baba; Tsutomu Hashimoto, both of Shin-nanyo, Japan

[73] Assignee: Toyo Soda Manufacturing Co., Ltd., Yamaguchi, Japan

[21] Appl. No.: 7,677

[22] Filed: Jan. 30, 1979

[30] Foreign Application Priority Data

Feb. 1, 1978 [JP] Japan .............................. 53-10192[U]

[51] Int. Cl.² ........................................... B01D 15/08
[52] U.S. Cl. ................................................ 210/198 C
[58] Field of Search .................... 210/31 C, 198 C

[56] References Cited

U.S. PATENT DOCUMENTS

| 3,504,799 | 4/1970 | Ogle | 210/198 C |
| 3,510,271 | 5/1970 | Emneus et al. | 210/198 C |
| 4,073,725 | 2/1978 | Takguchi | 210/198 C |

*Primary Examiner*—John Adee
*Attorney, Agent, or Firm*—Oblon, Fisher, Spivak, McClelland & Maier

[57] ABSTRACT

A gel permeation chromatograph system comprises a series of a solvent tank, a line filter and a distribution block; a pair of series of constant flow feeding pumps and sample injecting devices which are connected to the distribution block under dividing into a sample side passage and a reference side passage; a pair of analysis columns in each passage; and a detector connected to the outlet side passages of said analysis columns.

2 Claims, 3 Drawing Figures

(A)

INJECTION

PRESSURE ELEVATION (B)

(C)

DISCHARGE

GEL PERMEATION CHROMATOGRAPH SYSTEM

BACKGROUND OF THE INVENTION

1. Field of the Invention:

The present invention relates to a gel permeation chromatograph for analyzing a sample.

2. Description of the Prior Art

FIG. 1 shows a conventional gel permeation chromatograph system wherein a solvent tank (1), a line filter (2), a constant flow feeding pump (3) and a distribution block (4) are connected in series and it is divided at the distribution block into a sample side passage comprising a sample injector (5) and a sample analysis column (6) and a reference side passage comprising a reference side column and the other ends of these columns are connected to a detector (8).

The gel permeation chromatograph system for dividing a solvent fed from one constant flow feeding pump (3) into two passages has been used. There has been no trouble for a low speed gel permeation chromatograph which usually requires about 4 hours for the measurement of one sample. However, a high speed gel permeation chromatograph system which requires only about 20 to 40 minutes for its measurement has been commercialized depending upon a development of a gel permeation chromatograph carrier having high number of theoretical plates.

In the column having high number of theoretical plates, it is usual to fill in high density, high functional gel which has a particle size of 1/6 to 1/10 times of the particle size of the gel for the low speed gel permeation chromatograph system as the gel in the column.

In the case of the conventional gel permeation chromatograph system having the structure shown in FIG. 1 is used for measuring by such column filling the gel in high density, when a sample is fed into the analysis column (6) in a measurement of the sample having large molecular weight and wide molecular weight distribution, an inner pressure in the analysis column (6) is elevated by its viscosity effect (about 2 Kg/cm$^2$ in a case of injecting 2 ml of 0.3% of polyethylene having a molecular weight of several hundred thousand at 135° C.) whereby the solvent fed from the constant flow feeding pump (3) is distributed depending upon a ratio of the inner pressure of the analysis column (6) to that of the reference side column (7) and a large ratio of the solvent is fed to the reference side column (7) depending upon the ratio of the different inner pressures.

This phenomenon is remarkably found when the sample reaches to a column end filter at the inlet of the column and it passes through the filter. During the time passing the column after the column end filter, the sample is expanded in the column to reduce gradually the inner pressure. Accordingly, a quantative accuracy and a reproducibility of the chromatogram are decreased and a fluctuation of a base line and a shock at the injection of the sample are increased.

FIG. 2(A) shows a chromatogram of a polyethylene having a molecular weight of several hundred thousand in o-dichlorobenzene as a solvent by two columns connected in series at 135° C. The variations of the base line are found (a) at the time of the injection of the sample or (b) at about initiation of an elution to a discharge limit for the first column in a serial connections of plural columns. Moreover, the inner pressure of the column is gradually changed to cause (c) a step of the base line or a drift.

FIG. 2(B) shows a chromatogram under the variation of the inner pressure of the column from the initiation to the elution.

Such phenomena are remarkable when a differential refractometric densitometer having higher flow rate dependency that that of the other detector, is used as a detector for a gel permeation chromatograph system at a measurement of a gel permeation chromatogram at high temperature in which a flow rate balance highly affects to a stability of the base line.

SUMMARY OF THE INVENTION

It is an object of the present invention to provide a gel permeation chromatograph system which has a stable base line without a shock and has an improved quantative accuracy and an improved reproducibility.

The foregoing and other objects of the present invention have been attained by providing a gel permeation chromatograph system which comprises
- a series of a solvent tank (1), a line filter (2) and a distribution block (4);
- a pair of series of a constant flow feeding pumps (3), (3') and sample injecting devices (5),(5') which are connected to the distribution block (4) under dividing into a sample side passage and a reference side passage;
- a pair of analysis columns (9), (9') in each passage; and
- a detector (8) connected to the outlet side passages of said analysis columns (9),(9').

BRIEF DESCRIPTION OF THE DRAWINGS

FIG. 2(A) is a chromatogram resulted by the conventional gel permeation chromatograph system;

FIG. 2(B) is a chromatogram showing a variation of an inner pressure of a column from an injection of a sample to the elution;

FIG. 2(C) is a chromatogram given by the gel permeation chromatograph system of the present invention.

DETAILED DESCRIPTION OF THE PREFERRED EMBODIMENT

Figure 3:
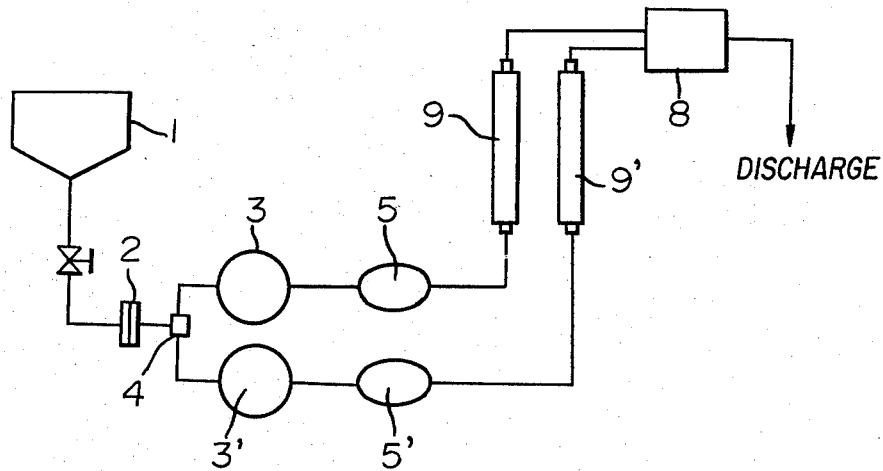
FIG. 3 is a diagram of one embodiment of a gel permeation chromatograph system of the present invention.

Referring to FIG. 3, one embodiment of the present invention will be illustrated. In the embodiment of the present invention, constant flow feeding pumps (3),(3') and sample injectors (5),(5') are independently connected to the sample side passage and the reference side passage whereby the excess flow rate in the reference side passage caused by the variation of the inner pressure of the column at the time injecting the sample is prevented. This can be used as a column switching type gel permeation chromatograph system.

Figure 1:
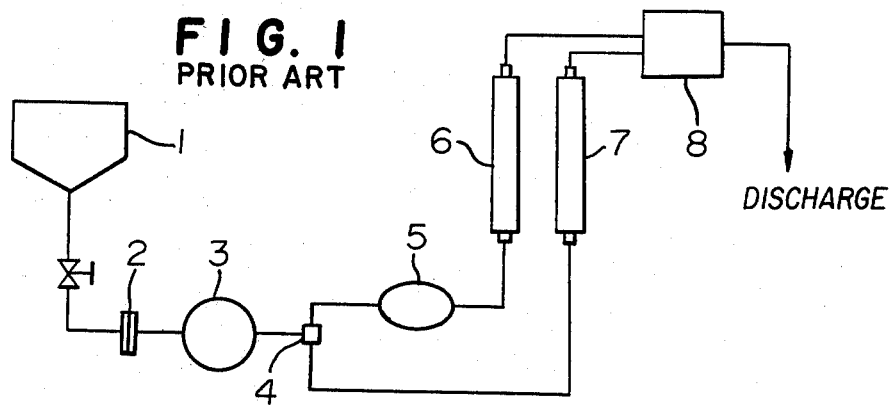
FIG. 1 shows a structure of the conventional gel permeation chromatograph system.
Figure 2:
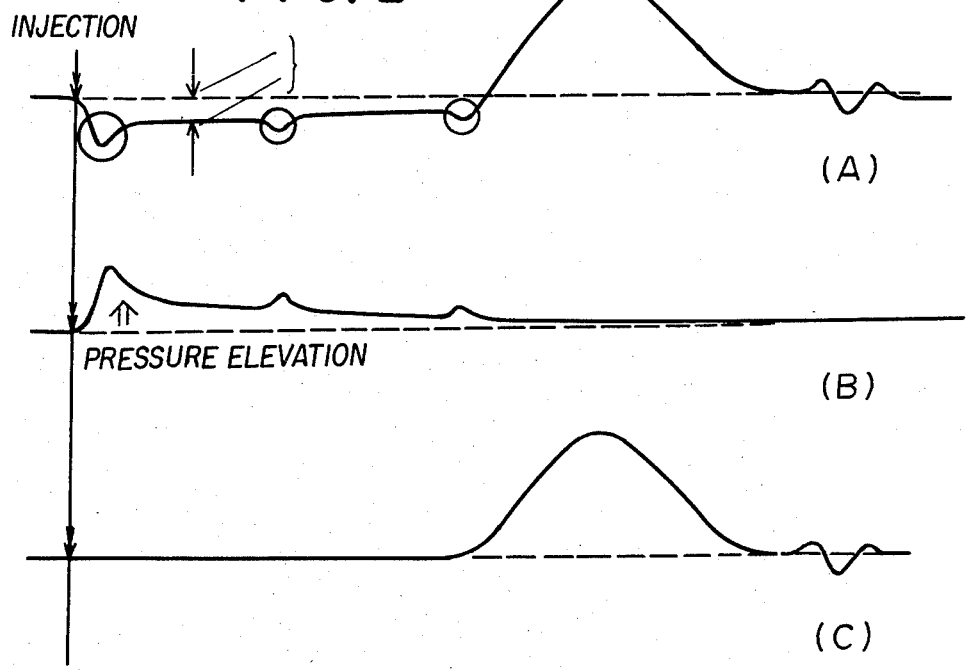
FIG. 2 shows certain chromatograms.

The chromatogram of the polyethylene having a molecular weight of several hundred thousand of that FIG. 2(A) measured by the gel permeation chromatograph system of the present invention is shown in FIG. 2(C). A feeding flow rate of the constant rate feeding pump (3) is not varied and the ratio of the flow rate of the reference side passage to that of the sample side passage is not varied to obtain a remarkably stable base line even though a load pressure is varied.

Moreover, a sample injector is equipped in the reference side passage, whereby it can be used as a column switching type gel permeation chromatograph system since either of the analysis column (9) in the sample side passage or the analysis column (9') in the reference side passage can be selected depending upon a molecular weight of the object polymer without using a switch valve used in the conventional system and the sample can be injected by either of the sample injector (5) or the sample injector (5').

What is claimed is:

1. A gel permeation chromatograph system which comprises:

a series of a solvent tank, a line filter and a distribution block;

a pair of series of constant flow feeding pumps and sample injecting devices which are connected in parallel to said distribution block for dividing into a sample side passage and a reference side passage;

a pair of analysis columns adapted to contain high density gel in each passage; and a detector connected to the outlet side passages of said analysis columns.

2. A gel permeation chromatograph system according to claim 1 wherein said columns are identical so that said system may be used as a column switching type gel permeation chromatograph system.

* * * * *